United States Patent [19]

Harris et al.

[11] 4,064,010

[45] Dec. 20, 1977

[54] PURIFICATION OF URICASE

[75] Inventors: Harry Wayne Harris, Hamlin; James Robert Schaeffer, Penfield; Roy Eugene Snoke, Webster, all of N.Y.

[73] Assignee: Eastman Kodak Company, Rochester, N.Y.

[21] Appl. No.: 707,458

[22] Filed: July 21, 1976

[51] Int. Cl.$^2$ .............................................. C12D 13/10
[52] U.S. Cl. ................................... 195/62; 195/66 R; 195/103.5 R
[58] Field of Search ............................... 195/62, 66 R

[56] References Cited

U.S. PATENT DOCUMENTS

| | | | |
|---|---|---|---|
| 3,431,176 | 3/1969 | Fukumoto et al. | 195/66 R |
| 3,475,276 | 10/1969 | Kano | 195/66 R |
| 3,620,923 | 11/1971 | Laboureur et al. | 195/66 R |
| 3,669,843 | 6/1972 | Aunstrup et al. | 195/66 R |
| 3,767,533 | 10/1973 | Sugisaki et al. | 195/66 R |
| 3,810,820 | 5/1974 | Laboureur et al. | 195/62 |

OTHER PUBLICATIONS

Cuatrecasas, "Affinity Chromatography of Macromolecules", in Advances in Enzymology, vol. 36, pp. 29–89, 1972.

*Primary Examiner*—Lionel M. Shapiro
*Attorney, Agent, or Firm*—Arthur L. Girard

[57] ABSTRACT

Catalase is effectively removed from a uricase preparation by amphiphilic chromotography using as the column material cyanogen bromide-activated polysaccharide having a hydrophobic ligand attached thereto. Particularly useful hydrophobic ligands are the alkanediamines.

14 Claims, No Drawings

PURIFICATION OF URICASE

FIELD OF THE INVENTION

This invention relates to the purification of uricase and especially to the effective removal of catalase from a uricase preparation.

BACKGROUND OF THE INVENTION:

Uricase is an enzyme capable of decomposing uric acid by catalyzing the oxidation to allantoin and hydrogen peroxide. This enzyme plays an important role in the medical field, especially in biochemical diagnosis where it is used as a reagent for the detection of uric acid in serum or urine.

Uric acid is one of the principle products of the catabolism of purine bases and of the materials which they contain, such as nucleic acids. If such catabolism does not take place or if elimination of the uric acid thus produced does not occur, accumulations of these products in the blood or body tissue can be the cause of many disorders, especially gout, certain forms of rheumatism, certain calculi in the region of the urinary system and various tissue changes, especially in the cardiovascular system. These disorders occur frequently because elimination of uric acid is rendered difficult by the very low solubility of this compound and increased concentrations of this compound due to any cause can bring about the formation of insoluble deposits.

Animal organs have heretofore been the principal source of uricase. Difficulties in extraction and purification of uricase from such sources have encouraged the development of uricase production from microorganisms. The production of uricase from various microorganisms, including bacteria, fungi and yeasts, is described in U.S. Pat. Nos. 3,431,176; 3,475,276; 3,620,923; 3,669,843; 3,767,533 and 3,810,820. It is likely that some trace of uricase might be found in any living organism but it cannot be predicted which organisms will yield uricase in sufficient quantities for any practical use.

U.S. Pat. Nos. 3,810,820 and 3,620,923 suggest that uricase may be obtained using bacteria of genus Micrococcus. However, no strians of bacteria of such genus have heretofore been identified as capable of providing useful levels of uricase in sufficient quantities to provide a commercially feasible source of uricase.

In the production of an enzyme such as uricase, whether by extraction from animal tissue or by fermentation of a microorganism, the desired enzyme is generally found in a liquid medium along with various other macromolecules such as proteins, including other enzymes, and/or other undersirable materials. Various methods have been used to purify the desired enzyme or separate it from at least some of the undesirable materials.

In purifying uricase, the enzyme, which is soluble in water but insoluble in organic solvents and insoluble in concentrated aqueous solutions of inorganic salts such as ammonium sulfate, can be recovered by precipitation either with an organic solvent which is miscible with water such as ethanol, methanol, isopropanol or acetone, or with a water soluble inorganic salt such as ammonium sulfate, mentioned previously. Salts or solvents can be removed by dialysis of a solution containing the redissolved precipitate.

Further purification can be accomplished, when necessary or desirable, by means of a series of precipitations from aqueous media, generally fractional precipitations, using organic liquids miscible with water or aqueous solutions containing ammonium sulfate. It is also possible to make use of adsorption upon hydroxyapatite, bentonite and alumina, and subsequent extraction, followed by elution using saline solutions. The purification can be carried still further by subjecting the thus treated products to chromatography, which may be a cyclic or noncyclic process, by making use of columns of substances which make it possible to eliminate those impurities, in particular, proteins, which are still present in the extract. The substances that have been suggested for this purpose include columns of cellulose ion exchange materials, dextrans and polyacrylamides. Elution may be effected by means of liquids in which there is a continuous or discontinuous change in the pH or in the molarity thereof.

Generally, even after such purification steps have been taken, the resulting uricase enzyme is not pure, but contains some amount of protein, e.g. other enzymes such as catalase. Catalase is a very undesirable interferant in a uricase preparation when the preparation is used for the quantitative analysis of uric acid in a peroxidase coupled detection system. The catalase catalyzes the decomposition of hydrogen peroxide and thus competes with the color forming reaction which is used to measure the quantity of uric acid present in a test solution. Prior to the present invention no purification methods were known to satisfactorily and efficiently separate catalase from uricase.

SUMMARY OF THE INVENTION:

The present invention provides a process for obtaining a stable, highly active uricase preparation from an enzyme preparation having catalase and uricase activities. Uricase preparations produced using conventional fermentation, extraction, purification, etc., techniques typically contain ~300–500 U of catalase per unit of uricase. Such enzyme preparations have generally been purified by treatment with ammonium sulfate. The process of the present invention involves the further purification of such preparations and comprises the step of passing the enzyme preparation having uricase and catalase activities through an amphiphilic chromatographic column. The chromatographic material in the column comprises cyanogen bromide-activated polysaccharide having a hydrophobic ligand attached thereto. The uricase and catalase are eluted separately by applying a discontinuous salt gradient in the presence of surfactant.

For the purposes of the present invention, the term catalase-free means that no detectable catalase, as measured by the procedure described hereinbelow, is present. By the term effectively free from catalase it is meant that a detectable amount of catalase activity may be present but that this amount is not sufficient to interfere with analytical results obtained using the uricase described herein in a coupled reaction as described above.

In one embodiment of the present invention, a catalase-free uricase preparation is produced by effectively removing catalase activity by applying a partially purified uricase preparation to a chromatographic column in which the hydrophobic ligand attached to the cyanogen bromide-activated polysaccharide is an alkanediamine. Hexanediamine is particularly preferred as the hydrophobic ligand.

DETAILED DESCRIPTION OF THE INVENTION

According to the present invention, a method is provided for obtaining a stable, highly active uricase preparation at least effectively free of catalase activity from uricase preparations containing both catalase and uricase activities.

Although the source of the uricase is not critical to the successful practice of the present invention, a particularly useful source of uricase is the soil microorganism *Micrococcus luteus*. A *Micrococcus luteus* culture yielding high levels of uricase is identified as NRRL B-8166 based on its deposit with the Argicultural Collection Investigations Fermentation Laboratory, Peroia, Illinois.

A taxonomic identification of the microorganism follows:

Description of *Micrococcus luteus* NRRL B-8166

Microscopy

Phase and light-field microscopy were performed with a LABOROLUX laboratory microscope (Leitz) using a magnification of 700 X.

Biochemical Tests

The gram stain, starch hydrolysis, indole, methyl red, catalase, oxidase, and $NO_3$-reduction tests were performed according to procedures of Blair et al "Manual of Chemical Microbiology," Williams and Wilkins, Co., Baltimore, Maryland, 1970. Sugar utilization was determined in commercially prepared medium or by adding 0.5% of filter-sterilized sugar solution (10% w/v) to sterile Durham tubes containing Phenol Red Broth Base (BBL). All tests were observed at 3-, 5-, and 7- day intervals.

Results

I. Microscopy
  A. Gram reaction - Gram-positive with a few gram-negative cells in older cultures.
  B. Morphology - Coccus, occurring mostly as single cells ca. 1μ in diameter with a few pairs and tetrads, non-motile.
II. Colony morphology
  A. Nutrient agar slant - yellow pigment, filiform, smooth, glistening.
  B. Nutrient agar plate -yellow pigment, circular, entire to serate, smooth, glistening, convex, raised colony.
  C. Gelatin agar - Light yellow, small, circular, wrinkled, granulated colony with slight liquification.
  D. Starch agar - Light yellow, small, smooth, round colony.
  E. Potato - Thin, glistening yellow growth.
III. Agar stab - yellow surface growth (strict aerobe).
IV. Nutrient broth - sediment, ropy, no pellicle.
V. Aerobic acid production in Phenol Red Broth
  A. Arabinose - negative
  B. Raffinose -negative
  C. Xylose - negative
  D. Lactose - slight acid, no gas after 7 days
  E. Fructose - negative
  F. Dulcitol - negative
  G. Glycerol - negative
  H. Maltose - negative
  I. Trehalose - negative
  J. Galactose - negative
  K. Mannitol - negative
  L. Sucrose - negative
  M. Adonitol - negative
  N. Glucose - slight to no acid, no gas after 5 days
VI. Hydrolysis of
  A. Gelatin - slow crateriform liquification
  B. Starch - negative (5 days)
  C. Casein - negative (5 days)
VII. Other biochemical tests
  A. Litmus milk - slightly acid, no coagulation (5 days)
  B. $H_2S$ formation - negative on SIM and TSI agar
  C. Phosphatase - positive
  D. Indole - negative (5 days)
  E. Methyl-red - negative (5 days)
  F. Catalase - positive
  G. Oxidase - negative
  H. Urea utilization - negative (5 days)
  I. $NO_3$ reduction - positive
  J. Growth on $NH_4H_2PO_4$ as a sole nitrogen source (4 days) - negative
  K. Growth in 5% NaCl - positive
  L. Growth in 15% NaCl - negative
  M. Growth at 45° C - negative
  N. Phenylalanine - negative This strain of *Micrococcus luteus* yields uricase preparations which demonstrate high levels of uricase activity on the order of above 1000 U/liter. The uricase from this microorganism is characterized by the following properties. It is a protein having a molecular weight of about 97,000 daltons. The uricase has maximum enzyme activity at pH 8.6 when using KPi buffer (potassium phosphate), and has a Michaelis constant of $3.7 \times 10^{-5}$ M and an inhibition constant of $4.5 \times 10^{-6}$ for oxonate. Cations inhibit the activity of this uricase. $Co^{+2}$ and $Mn^{+2}$ have a greater inhibitory effect than $Cu^{+2}$. A biphasic inhibitory response rate curve for the cations $Co^{+2}$ and $Mn^{+2}$ is also found. The uricase shows some activation in the presence of phosphate or sulfate anions. After purification as described herein, the uricase exhibits a specific activity of at least about 10.6 U per mg of protein.

A growth medium for cultivating the microorganism consists of the following nutrients; the concentration given based on one liter of medium is:

| | | |
|---|---|---|
| dibasic potassium phosphate | 2.0 | g/l |
| uric acid | 5.0 | g/l |
| yeast extract | 5.0 | g/l |
| acetic acid | 5.0 | g/l |
| salt solution | 10.0 | ml/l | where the salt solution consists of the following salts dissolved in water; the concentration in grams per liter of water is:

| | |
|---|---|
| $MgSO_4 \cdot 7H_2O$ | 0.25 |
| $MnSO_4 \cdot H_2O$ | 0.17 |
| $FeSO_4 \cdot 7H_2O$ | 0.028 |
| NaCl | 0.0006 |
| $CaCl_2 \cdot 2H_2O$ | 0.001 |
| $ZnSO_4 \cdot 7H_2O$ | 0.0006 |

Of course the growth medium may be adjusted and modified by those skilled in the art in order to optimize the production of uricase. A temperature of about 30° C is useful for growing the bacteria cells.

After the cells are grown, they are separated from the fermentation broth by centrifugation or other suitable means. Yields of 0.014 to 0.016 g of cells (wet weight) per ml. growth medium have been obtained.

Uricase is extracted from the cells by suspending the cells in potassium phosphate (KPi) buffer containing ethylenediamine tetraacetic acid (EDTA). Generally, an extraction pH of about 8.6 has been found satisfactory, although the extraction may be successfully performed at higher or lower pH levels. To lyse the cells, aliquots of the suspension, cooled in a brine-ice bath, were sonicated using an ultrasonic probe. The disrupted cells were centrifuged to separate cell debris. The average yield of uricase, located in the supernatant fraction, was about 22 units per gram of cells (wet weight). The uricase extracted from the cells can be partially purified by conventional techniques such as ammonium sulfate fractionation, TEAE-cellulose chromatography and diafiltration. Such conventional purification techniques leave the uricase preparation with high levels of catalase activity which make the preparation generally unsuitable for analytical techniques that use a peroxidase coupled detection system.

Other sources of uricase and the methods for obtaining similar uricase preparations are described in U.S. Pat. Nos. 3,431,176; 3,475,276; 3,669,843 and 3,767,533.

According to the present invention, the uricase and catalase activities can be separated by amphiphilic chromatography using a cyanogen bromide-activated polysaccharide having a hydrophobic ligand attached thereto. Hydrophobic ligands useful in the practice of this invention include the alkanediamines. Examples of such useful alkanediamines include ethanediamine, butanediamine, hexanediamine, etc. A particularly preferred hydrophobic ligand useful for separating catalase from uricase is hexanediamine, especially 1,6-hexanediamine.

Chromatographic materials useful in the practice of the present invention can be made by treating an aqueous suspension of a polysaccharide with cyanogen bromide and then reacting with the desired ligand such as, for example, an alkanediamine. The procedure is described in more detail in the examples which follow. A 4% by weight aqueous suspension of the polysaccharide has been found suitable for accomplishing the treatment with cyanogen bromide.

Generally, treatment of the polysaccharide with at least 1 gram of cyanogen bromide per gram of polysaccharide provides material which, after attaching the hydrophobic ligand, can be used to separate catalase from uricase. It is preferred, however, that the polysaccharide be activated by treatment with at least 6 grams of cyanogen bromide per gram of polysaccharide.

A commercially available material sold by Pharmacia Fine Chemicals as AH-Sepharose ® 4B (a cyanogen bromide-activated polysaccharide having a 1,6-hexanediamine ligand attached at the active sites) is useful in removing catalase from uricase. This material has a nitrogen content of 2.5%. Although the specific relevance of the nitrogen content of the chormatographic material to its performance in this invention is unknown, it is apparent that materials with higher nitrogen content are more effective in separating catalase from uricase. As indicated by Table III, this material is effective in removing 79% of the catalase activity while recovering substantially all of uricase activity.

A material prepared by modifying Sepharose ® 4B (a polysaccharide available from Pharmacia Fine Chemicals) by treatment with 6 grams of cyanogen bromide per gram of Sepharose ® 4B and then attaching 1,6-hexanediamine to the activated sites has been found effective in removing all detectable catalase from a uricase to produce a catalase-free uricase preparation. (See Table II.) This modified Sepharose ® 4B material has been found to have a nitrogen content of 6.7%.

To separate the uricase from catalase using amphiphilic chromatography, an ammonium sulfate pellet containing both uricase and catalase activities is dissolved in a buffered 50 mM KPi (potassium phosphate) solution. Generally, the solution is buffered to a pH in the range of from about 6 to about 10, although a pH of about 8.6 is preferred. After equilibrating the column with the KPi buffer, the dissolved sample is applied to the column. The column is then washed with four column volumes of the buffer. The uricase is eluted using a solution of 0.5 M sodium chloride in the KPi buffer containing $10^{-4}$ M EDTA (ethylenediaminetetraacetic acid) and 0.5 percent (v/v) Tergitol 15-S-7, a nonionic surfactant which is a polyethylene glycol ether of linear alcohol available from Union Carbide Corporation. After two elutions, each consisting of 2 column volume aliquots of the above salt and detergent solution, the combined fraction was assayed for total enzyme activity and the assay shows that about 80 percent of the uricase activity was recovered. No measurable catalase activity was found in the uricase fraction.

The catalase was eluted separately using a salt and detergent solution containing 2.0 M sodium chloride in KPi buffer having $10^{-4}$ M EDTA and 0.5% (v/v) Tergitol 15-S-7. The combined fraction was assayed for total enzyme activity and the assay showed that substantially all of the catalase was eluted.

The uricase solution obtained after purification can be freeze-dried or lyophilized for long term storage. A stable powdered uricase perparation is thus obtained, even without the use of added stabliizers.

The uricase preparation of this invention is useful for assaying for uric acid, particularly when using assay methods which use a hydrogen peroxide detection system. Additional advantages will be appreciated by those skilled in the art upon consideration of the following examples which further illustrate the invention.

MAINTENANCE OF THE CULTURE

Isolated colonies of *Micrococcus luteus* NRRL B-8166 were transferred to agar slants containing nutrient medium comprising glucose, 1% yeast extract and 10 ml basal salt solution. The basal salt solution contained

|  | Grams/liter |
|---|---|
| $MgSO_4 \cdot 7H_2O$ | 25.0 |
| $MnSO_4 \cdot H_2O$ | 17.0 |
| $FeSO_4 \cdot 7H_2O$ | 2.8 |
| NaCl | 0.06 |
| $CaCl_2 \cdot 2H_2O$ | 0.10 |
| $ZnSO_4 \cdot 7H_2O$ | 0.06 |

The slants were incubated for 2 days at 30° C and then stored at 4° C until used.

EXAMPLE 1:

Growing Microorganism to Produce Uricase

A slant of *Micrococcus luteus* NRRL B-8166 was transferred to a 125 ml. flask containing 25 ml. of growth medium. The growth medium contained, per liter of medium,

| Dibasic potassium phosphate | 2 | g |
| Uric acid | 5 | g |
| Yeast extract | 5 | g |
| Acetic acid | 5 | g |
| Basal salt solution | 10 | ml |

The pH value was adjusted to 7.0 with KOH. The cells were grown for 24 hours at 30° C with shaking at 200 rpm (2 inch throw) and then transferred to one liter flasks containing 500 ml medium. The cells were grown for 22 hours at 30° C with shaking at 100 rpm and then collected by centrifugation at 13,700 × g for 15 minutes. The yield was 0.014 - 0.016 g cells (wet weight) per ml. growth medium.

A 10% (w/v) suspension of cells in 50 mM potassium phosphate (KPi) buffer, pH 8.6, containing $10^{-4}$M ethylene-diamine tetraacetic acid (EDTA) was prepared. To lyse the cells, 50 ml aliquots of the suspension, cooled in a brine-ice bath, were sonicated for 10 minutes using a probe with standard tip (Ultrasonics, Inc., Plainview, New Jersey) powered by a J-17A power supply operating at setting 5 (Branson Sonic Power Co., Danville, Connecticut). The disrupted cells were centrifuged at 27,000 × g to precipitate cell debris. The average yield of uricase, located in the supernatant fraction, was 22 units per g cells (wet weight).

Making Modified Sepharose ® 4B Chromatographic Column Material by Immobilization of 1,6-Hexanediamine of Agarose A stirred slurry of 100 ml agarose (a polysaccharide available commercially as Sepharose ® 4B from Pharmacia Fine Chemicals) and 100 ml of distilled water was cooled in an ice bath to 20° C and the pH was adjusted to 11 with 6 M sodium hydroxide, 24 g of cyanogen bromide (~250 mg/ml) was added to the slurry and the pH was maintained at 11±0.2 by dropwise addition of 6 M sodium hydroxide. Ice was added directly to the reaction mixture as needed to maintain the temperature at 20°±4° C. The reaction mixture was stirred for 30 minutes (addition and reaction time) and the solid product was recovered by vacuum filtration on a sintered glass funnel. The product was washed with cold 0.1 M potassium phosphate buffer adjusted to pH 10. The cyanogen bromide activated agarose was added to 300 ml of 0.1 M phosphate buffer (pH 10) containing (0.05 mole) 1,6-hexanediamine. The reaction mixture was stirred for 24 hours at 4° C. The solid product was collected by vacuum filtration, washed with a liter of distilled water, and added to 100 ml of the potassium phosphate buffer containing 20 ml of ethanolamine. The slurry was stirred for 24 hours at 4° C. The product was collected, washed with distilled water until the wash was free of amine (using the 2,4,6-Trinitrobenzene Sulfonate test) and stored in the refrigerator in 100 ml of the potassium phosphate buffer.

EXAMPLE 2

Purification of Enzyme Solution

A. Ammonium Sulfate Fractionation - All subsequent steps were performed at 4° C. Solid ammonium sulfate (0.351 g/ml) was added slowly with stirring to the enzyme solution prepared in Example 1. After 1 hour, the material was centrifuged at 27,000 × g for 20 minutes. Enzyme was in the supernatant fraction (I). Ammonium sulfate (0.141 g/ml) was added to this fraction, and after 1 hour, the sample was centrifuged as before. Both uricase and catalase activities were contained in the pellet fraction (II); this material was then dissolved in 0.22 ml KPi buffer, pH 8.6, per ml of original volume of fraction I.

B. Amphiphilic Column Chromatography - In order to remove the unwanted catalase activity, the solution containing the redissolved ammonium sulfate pellet was chromatographed by amphiphilic column chromatography using the 1,6-hexanediamineagarose material as prepared above.

The dissolved ammonium sulfate pellet was diluted with four volumes of 50 mM KPi at a pH of 8.6 containing $10^{-4}$EDTA. The dilute solution was applied to a 2.8 cm × ]cm column of the 1,6-hexanediamine-agarose equilibrated with KPi buffer. The column was washed with four column volumes of this buffer. Next the column was eluted twice, each time with two column volume aliquots of 0.5 M NaCl in KPi buffer containing $10^{-4}$ EDTA and 0.5% (v/v) Tergitol 15-S-7. Approximately 80% of the uricase activity was assayed in the combined fractions. Finally the column was eluted with four column volumes of 2.0 M NaCl in the KPi-EDTA-Tergitol buffer solution. The combined fractions for this elution contained no detectable uricase and substantially all the catalase activity of the crude enzyme solution.

C. TEAE-Cellulose Chromatography - The fractions containing uricase were diluted with KPi-EDTA buffer, pH 8.6, to a final salt concentration of 0.3 M NaCl and applied to a triethylaminoethyl-cellulose column (2.8 cm × 9 cm). Uricase was eluted from the column with two column volumes of KPi-EDTA buffer, pH 8.6, containing 0.5 M NaCl. This sample, free of surfactant, was concentrated in an Amicon diaflo cell fitted with a PM-10 membrane, and then dialyzed overnight against the KPi-EDTA buffer, pH 8.6. This enzyme preparation can be freeze-dried (lyophilized) and stored as a dry powder until ready for use.

A representative isolation of uricase purified according to the above procedure, but using two ammonium sulfate fractionation steps, is presented in Table I. The overall recovery of this purification process was 73 percent of the starting uricase activity.

Table I

| | Purification of Uricase From Micrococcus Luteus | | | | |
|---|---|---|---|---|---|
| | Total Units | | Uricase Recovery | Uricase Specific Activity | Protein |
| Sample | Uricase | Catalase | % | U per mg Protein | mg/ml |
| Sonicated Supernatant | 663 | 1,125,517 | 100 | 1.20 | 1.62 |
| Ammonium Sulfate I | 542 | 251,438 | 82 | —[a] | —[a] |
| Ammonium Sulfate II Hexanediamine-Agarose | 490 | 288,000 | 74 | 2.87 | 1.96 |

Table I-continued

| Sample | Purification of Uricase From Micrococcus Luteus | | | | |
|---|---|---|---|---|---|
| | Total Units | | Uricase Recovery % | Uricase Specific Activity U per mg Protein | Protein mg/ml |
| | Uricase | Catalase | | | |
| Column Eluate TEAE-Cellulose | 543 | 0 | 82 | —[a] | —[a] |
| Column Eluate | 484 | 0 | 73 | 10.6 | 0.122 |

[a]Samples not analyzed

ASSAY OF URICASE

Uricase was assayed spectrophotometrically by following the disappearance of uric acid at 290 nm using a modification of the procedure described by Mahler et. al, J. Biol. Chem., 216, p. 625, (1955). Assay tubes contained 2.7 ml 50 mM KPi buffer pH 8.6, 0.1 mM sodium EDTA, 0.05 ml 6 mM urate, plus enzyme and water to give a final volume of 3.0 ml. Changes or additions to the assay mixtures were made when necessary. Tubes were incubated for 5 minutes at 30° C; the reaction was started by adding enzyme. Molar extinction coefficient for uric acid at 290 nm is 12,300. Activity was expressed in units of uricase activity, where a unit is that amount of enzyme which catalyzes the oxidation of one $\mu$mole of uric acid per minute at 30° C and pH 8.6.

ASSAY OF CATALASE

Catalase was assayed according to the procedure described in Worthington Enzyme Manual, Worthington Biochemical Corporation, Freehold, New Jersey, p. 41 (1972).

EXAMPLE 3

Removal of Catalase from a Partially Purified Uricase Preparation Using Modified Sepharose 4B A 2.8 × 9 cm column (55 ml bed volume) containing 1,6-hexanediamine modified Sepharose ® 4B prepared according to the above procedure was equilibrated at 4° C with 50 mM potassium phosphate buffer containing $10^{-4}$ M EDTA having a pH of 8.6.

A 25 ml volume of ammonium sulfate-treated bacterial uricase preparation according to the procedure in Example 2, part A, was diluted with 200 ml of the same buffer, and 198 ml was applied to the polysaccharide column. The column was washed with 200 ml buffer, then eluted with 200 ml of 0.5 M sodium chloride in the above potassium phosphate-EDTA buffer containing 0.5% Tergitol 15-S-7 and re-equilibrated with buffer. The fractions were then assayed for uricase and catalase activities.

Table II shows that uricase, free of catalase, was recovered in 75% yield from fractions 1 and 2.

Table II

| Sample | Purification of Bacterial Uricase Using Modified Sepharose 4B | | | | |
|---|---|---|---|---|---|
| | Volume (ml) | Activity (U) | | % Recovery | |
| | | Uricase | Catalase[a] | Uricase | Catalase |
| Initial Sample Placed on Column | 198 | 208.6 | 60,188 | 100 | 100 |
| Effluent | 200 | | | | |
| Wash | 200 | | | | |
| Fraction 1 | 150 | 130.0 | 0 | 62 | 0 |
| Fraction 2 | 100 | 26.1 | 0 | 13 | 0 |
| TOTAL (Fraction 1+2) | | 156.1 | 0 | 75 | 0 |
| High Salt Fraction | 200 | 0 | 85,493 | 0 | 100 |

EXAMPLE 4

Removal of Catalase from a Partially Purified Uricase Preparation Using AH-Sepharose ® 4B A 0.5 × 4 cm test column (~0.5 ml bed volume) containing AH-Sepharose ® 4B (Pharmacia Fine Chemicals) was prepared and equilibrated with 50 mM postassium phosphate-EDTA buffer at pH 8.6 and 4° C as in Example 3.

A 1 ml volume of bacterial uricase preparation partially purified with ammonium sulfate treatment as in Example 3, was added to the column and eluted sequentially with 2.0 ml of 0.15 M NaCl, 1.5 ml of 0.2 M NaCl and 1.8 ml of 0.5 M NaCl in potassium phosphate-EDTA buffer containing 0.5% Tergitol 15-S-7. The fractions were then assayed for uricase and catalase activites as above. Results, shown in Table III, indicate that this column did not completely separate the catalase activity from that of uricase; all of the uricase activity was recovered while 72% of the catalase activity was eliminated.

Table III

| Sample | Purification of Bacterial Uricase Using Commercially Available AH-Sepharose ® 4B | | | | |
|---|---|---|---|---|---|
| | Volume (ml) | Activity (U) | | % Recovery | |
| | | Uricase | Catalase | Uricase | Catalase |
| Initial Sample Placed on Column | | 3.5 | 5793 | | |
| Effluent | 3.5 | 0 | 0 | 0 | 0 |
| Fraction 1 | 2 | 1.95 | 264 | 56 | 5 |
| Fraction 2 | 1.5 | 1.62 | 938 | 46 | 16 |
| Fraction 3 | 1.8 | 0.25 | 2979 | 7 | 51 |
| TOTAL | | 3.82 | 4181 | 109% | 72% |

ELEMENTAL NITROGEN ANALYSIS OF MODIFIED SEPHAROSE ® 4B AND COMMERCIALLY AVAILABLE AH-SEPHAROSE ® 4B

The nitrogen content of the two materials, modified Sepharose ® 4B prepared according to the above procedure and commercially available AH-Sepharose ® 4B, was determined in the following manner.

A 5 g sample of AH-Sepharose ® 4B was washed with a liter of 0.15 M aqueous sodium chloride solution followed by a liter of distilled water to wash out any inert solids remaining in the material. The solids were stirred in 30 ml of dioxane containing 15 g ethanolamine overnight at room temperature to react any remaining reactive functions in the polymer. The product was collected by vacuum filtration and washed with distilled water then dioxane until the wash was shown to be free of amine. The product was then washed with 2 liters of distilled water and lyophilyzed. Elemental nitrogen analysis of the treated materials showed:

AH-Sepharose ® 4B - 2.5% nitrogen
Modified Sepharose ® 4B - 6.7% nitrogen

The invention has been described in detail with particular reference to certain preferred embodiments thereof, but it will be understood that variations and modifications can be effected within the spirit and scope of the invention.

We claim:

1. A process for separating uricase from catalase comprising:
    applying a uricase preparation having uricase and catalase activities to a chromatographic column comprising a cyanogen bromide-activated polysaccharide material having a hydrophobic ligand attached thereto, thereby leaving the uricase and the catalase on the column, and
    eluting the uricase from the column separately from the catalase to obtain a uricase preparation that is effectively free from catalase.

2. The process of claim 1 wherein the uricase is eluted with a 0.5 M salt solution comprising a surfactant and ethylenediamine tetraacetic acid, and buffered at a pH in the range of from about 6.0 to 10.

3. The process of claim 2 wherein the salt solution is buffered at a pH of 8.6.

4. The process of claim 1 which further includes eluting the catalase separately from the column.

5. The process of claim 4 wherein the catalase is eluted with a 2.0 M salt solution comprising a surfactant and buffered at a pH in the range of from about 6.0 to about 10.0.

6. The process of claim 1 wherein the hydrophobic ligand is an alkanediamine.

7. The process of claim 6 wherein the alkanediamine is hexanediamine.

8. A process for effectively removing catalase from a uricase preparation obtained by growing Micrococcus leuteus NRRL B-8166, which process comprises chromatographing a buffered solution of the uricase on a column comprising a cyanogen-bromide activated polysaccharide having a hydrophobic ligand attached thereto and eluting the uricase from the column separately from the catalase.

9. A process for purifying and effectively removing catalase from a uricase preparation obtained by growing Micrococcus luteus NRRL B-8166, which process comprises:
    precipitating the uricase from solution with ammonium sulfate to obtain an ammonium sulfate pellet;
    dissolving the pellet in a buffer solution;
    applying the buffer solution containing the dissolved pellet to a chromatographic column comprising a cyanogen-bromide activated polysaccharide material having a hydrophobic ligand attached thereto, thereby retaining the uricase on the column;
    eluting the uricase from the column using a salt, surfactant, buffer solution to obtain an eluted uricase solution;
    applying the eluted uricase solution to a triethylaminoethyl-cellulose chromatographic column, thereby retaining the uricase on the column;
    eluting the uricase from the triethylaminoethyl-cellulose column using a buffered salt solution; and
    dialyzing the buffered salt solution containing the uricase to obtain a purified uricase solution.

10. The process of claim 9 wherein the hydrophobic ligand is an alkanediamine.

11. The process of claim 10 wherein the alkanediamine is hexanediamine.

12. A uricase preparation effectively free from catalase activity produced by purifying a uricase preparation obtained by growing *Micrococcus luteus* NRRL B-8166, the purification steps comprising:
    precipitating the uricase from a solution of the uricase preparation with ammonium sulfate to obtain an ammonium sulfate pellet;
    dissolving the pellet in a buffer solution and applying it to a chromatographic column comprising a cyanogen-bromide activated polysaccharide material having a hydrophobic ligand attached thereto, thereby leaving the uricase on the column;
    eluting the uricase from the column using a salt, surfactant, buffer solution to obtain an eluted uricase solution;
    applying the eluted uricase solution to a triethylaminoethyl-cellulose chromatographic column, thereby leaving the uricase on the column;
    eluting the uricase from the triethylaminoethyl-cellulose column using a salt, buffer solution to obtain a second eluted solution; and
    dialyzing the second eluted solution to obtain said uricase preparation.

13. The uricase preparation of claim 12 which is lyophilized to form a dry powder.

14. A process for producing a catalase-free uricase preparation, said process comprising chromatographing a buffered solution of an enzyme preparation having catalase and uricase activity on a column comprising a cyanogen bromide-activated polysaccharide having a 1,6-hexanediamine ligand attached thereto, said polysaccharide having an elemental nitrogen content of at least 6.7 percent, and eluting the uricase from the column.

* * * * *